(12) United States Patent
Elkins et al.

(10) Patent No.: US 7,056,339 B2
(45) Date of Patent: Jun. 6, 2006

(54) DRUG DELIVERY PLATFORM

(75) Inventors: Christopher J. Elkins, Redwood City, CA (US); Michael D. Dake, Stanford, CA (US); Jacob M. Waugh, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 643 days.

(21) Appl. No.: 10/101,455

(22) Filed: Mar. 11, 2002

(65) Prior Publication Data

US 2003/0004564 A1    Jan. 2, 2003

Related U.S. Application Data

(60) Provisional application No. 60/285,383, filed on Apr. 20, 2001.

(51) Int. Cl.
*A61F 2/06* (2006.01)

(52) U.S. Cl. .................................... 623/1.46
(58) Field of Classification Search ............ 606/194, 606/195, 198; 623/1.11–1.15, 1.46, 1.44
See application file for complete search history.

(56) References Cited

U.S. PATENT DOCUMENTS

| | | | |
|---|---|---|---|
| 5,603,722 A * | 2/1997 | Phan et al. ............ | 623/1.15 |
| 5,697,967 A | 12/1997 | Dinh et al. | |
| 5,891,108 A | 4/1999 | Leone et al. | |
| 5,916,597 A * | 6/1999 | Lee et al. ............. | 623/1.15 |
| 5,972,027 A | 10/1999 | Johnson et al. | |
| 6,004,346 A | 12/1999 | Wolff et al. | |
| 6,071,305 A | 6/2000 | Brown et al. | |
| 6,096,070 A | 8/2000 | Ragheb et al. | |
| 6,273,913 B1 * | 8/2001 | Wright et al. .......... | 623/1.15 |
| 6,280,411 B1 | 8/2001 | Lennox et al. | |
| 6,335,029 B1 | 1/2002 | Kamath et al. | |
| 6,774,278 B1 * | 8/2004 | Ragheb et al. ......... | 623/1.15 |

FOREIGN PATENT DOCUMENTS

| | | |
|---|---|---|
| EP | 074069 A3 | 12/1996 |
| EP | 0747069 A2 | 12/1996 |

OTHER PUBLICATIONS

Ettenson, D. et al., Local Drug Delivery: an Emerging Approach in the Treatment of Restenosis, Vascular Medicine, (2000), vol. 5:97-102.
Gunn, J. et al., Stent Coatings and Local Drug Delivery State of the Art, European Heart Journal, (1999), vol. 20: 1693-1700.
Raman, K. et al., Coated Stents: Local Pharmacology, Sernin Intervent Cardiol, (1998), vol. 3: 133-137.

* cited by examiner (Continued)

*Primary Examiner*—Vy Bui
(74) *Attorney, Agent, or Firm*—Pamela J. Sherwood; Bozicevic, Field & Francis, LLP

(57) ABSTRACT

A stent based drug delivery system. A biological agent of interest is entrapped within a matrix, which is loaded into channels on the surface of a stent. The matrix allows for release, usually sustained release, of the entrapped agent. The stent and matrix is sheathed with a covalently bound gel. In one embodiment of the invention, the stent is used to deliver therapeutic agents to a patient, providing the advantage of efficient delivery and sustained release of an agent at a localized site. In another embodiment of the invention, the drug delivery system is used for testing and comparison of candidate drugs in an in vivo setting.

48 Claims, 6 Drawing Sheets

DRUG DELIVERY PLATFORM

CROSS-REFERENCE TO RELATED APPLICATIONS

This application claims the benefit of priority from U.S. Provisional application No. 60/285,383, filed Apr. 20, 2001.

BACKGROUND OF THE INVENTION

Stents and other prosthetic devices have provided the means to clinically treat many conditions. Stents are commonly used to open blood vessels, e.g. clearing obstructions, preventing restenosis, providing support at the site of an aneurysm, and to repair damage to vascular tissues, e.g. arteries and veins. In addition to blood vessels, other vessels of the body may be repaired with a stent, including the trachea for breathing disorders, renal and urethral tubules, fallopian tubes for the treatment of infertility, eustachian tubes for the treatment of chronic ear infection and other hearing disorders, large and small intestines where the vessels may be occluded with tumor cells, etc.

Many stent designs are known and in clinical use. For example, they can be cut from a tube or formed from a wire that has been bent back and forth in a zig-zag pattern and wound in a circumferential direction to form one or more loops of a pre-determined circumference. Typically, the stent is radially expandable from a collapsed condition. Once in position, it is expanded to the predetermined size, to support and reinforce the lumen.

One of the largest fields for the use of stents is in the treatment of cardiovascular disease. Treatment by balloon angioplasty, percutaneous transluminal angioplasty (PTA), has been shown to improve life expectancy after occlusion of blood vessels, but up to 40% of patients encounter restenosis within 6 months. Since angioplasty alone is marked by progressive luminal compromise (negative remodeling), stenting has become the leading interventional strategy with current application in 60–70% of PTAs. Stent use offers a number of advantages over simple PTA, including decreased early in-hospital complications, increase in luminal diameter, decreased negative remodeling, and sealing of intimal flaps. However, arteries treated with stents also encounter dramatically accelerated rates of in-stent restenosis, which are clinically significant in up to 40% of cases. Smooth muscle proliferation and vascular remodeling; restenosis after stent deployment is due almost entirely to smooth muscle hyperplasia and matrix proliferation. In-stent neointima formation thus remains a major procedural limitation for stent use, limiting both utilization and long-term clinical benefits.

There has been interest in the development of a drug delivery platform that can provide local delivery of pharmaceuticals, for example, the delivery of anti-restenotic drugs; anti-proliferative agents for the treatment of tumors; antibiotics in the treatment of chronic ear infection, and the like. While systemic administration of drugs or other biologically-active substances is satisfactory for some medical treatments, many other treatments can be facilitated and/or improved with local drug delivery or administration to selected portions of internal body tissues. Localized drug administration is particularly advantageous where drug retention in the treated locus is required for an effective period of time without appreciably affecting other body tissues The development of stents for drug delivery is of great interest for the treatment of a variety of conditions. The present invention addresses this problem.

Relevant Art

U.S. Pat. No. 6,004,346, "Intralumenal drug eluting prosthesis" discloses a drug eluting stent. U.S. Pat. No. 5,972,027 discloses a porous stent drug delivery system. A drug eluting stent is described in U.S. Pat. No. 5,697,967. U.S. Pat. No. 6,335,029 is directed to polymeric coatings for controlled delivery of active agents. Other coatings for localized delivery of drug agents are disclosed in U.S. Pat. No. 6,280,411. Brown et al., U.S. Pat. No. 6,071,305 relates to a directional drug delivery stent. A drug delivery stent for liquid formulations is disclosed by Leone et al., U.S. Pat. No. 5,891,108.

Reviews of the field of local drug delivery, and the treatment of restenosis may be found in Ettenson and Edelman (200) *Vasc Med* 5(2):97–102; Gunn and Cumberland (1999) *Eur Heart J* 20(23):1693–700; and Raman and Edelman (1998) *Semin Interv Cardiol* 3(3–4):133–7; among others.

SUMMARY OF THE INVENTION

Compositions and methods are provided for a stent based drug delivery system. The stent comprises a matrix, where the matrix has entrapped a pharmaceutical agent of interest. The matrix, for example microspheres, etc. resides within a channel formed on one or both of the abluminal or adluminal surfaces of the stent, and allows for release, usually sustained release, of the entrapped agent. The stent and matrix is encased with a gel covalently bound to the stent surface and optionally also covalently bound to the matrix, which prevents loss of the matrix during transport and implantation of the stent, and which affects the release of the biologically active agent, through degradation and diffusion characteristics.

The delivery system of the invention finds use in the delivery of pharmaceutical agents, particularly where a localized concentration of the agent is desirable. In one embodiment, the stent is a cardiovascular stent, where the pharmacologic agent is an anti-restenotic agent, e.g. to prevent in-stent restenosis. In another embodiment, the stent is a gastrointestinal stent that prevents obstruction due to tumor ingrowth or reactive hyperplasia, and which also delivers a chemotherapeutic agent for treatment of hyperplasia.

The delivery system of the invention also find use in the evaluation of candidate agents by providing both efficient delivery and low perturbation at the site of implantation. The efficiency of drug delivery provided by the drug delivery stent allows a sensitive comparison of the effect of an agent on, for example, restenosis, hyperplasia, and the like.

In one embodiment of the invention, the matrix is formed into microspheres or other discrete particles that entrap the agent to be delivered. The matrix may be biodegradable, bioerodible, or biocompatible, non-biodegradable compositions. In all cases the matrix will provide for release of the entrapped agent over time. The matrix is loaded into the channels, and then ensheathed in a gel bound to the stent surface, e.g. by derivatization of a metal oxide surface with methoxysilane, by binding to a plastic surface, binding to a biodegradable or bioerodible stent surface, and the like. The pharmaceutical agent is not directly bound to the stent surface.

DETAILED DESCRIPTION OF THE EMBODIMENTS

Figure 1A:
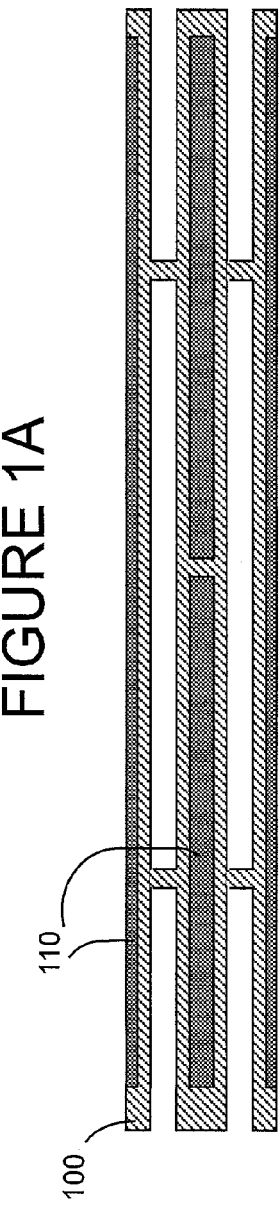
FIG. 1A is a diagram of a channeled stent.
Figure 1B:
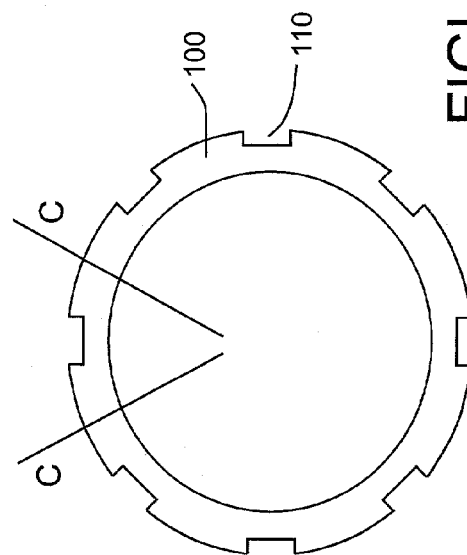
FIG. 1B is a cross-sectional view of the stent and channels.
Figure 1C:
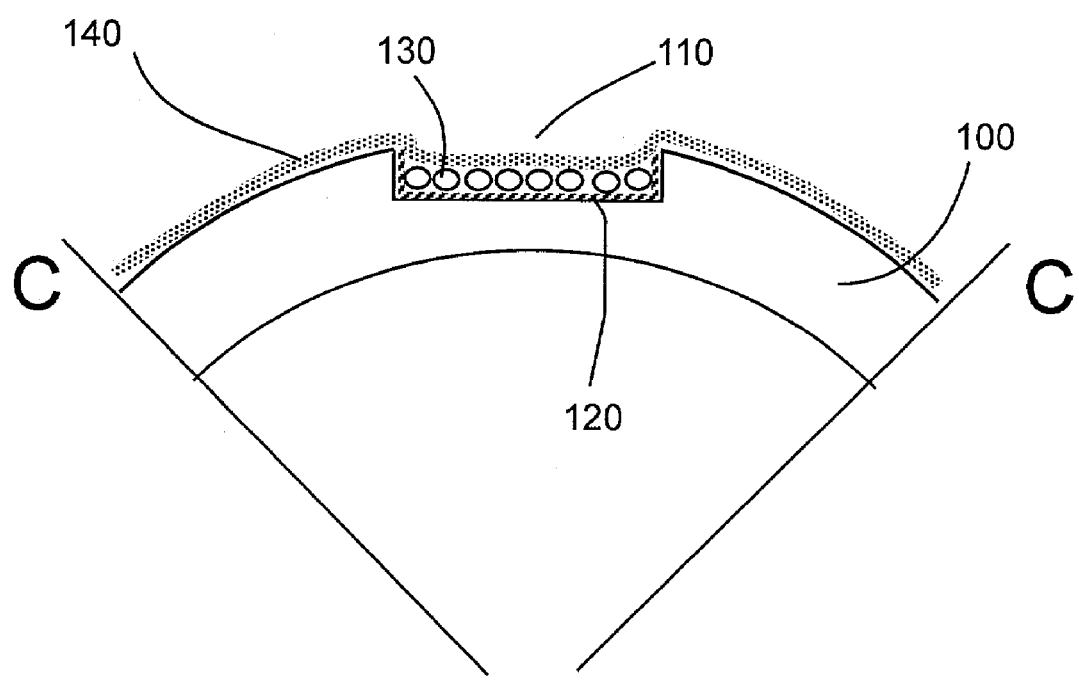
FIG. 1C is a close-up view of the stent.

Compositions and methods are provided for a stent based drug delivery system. As shown in FIGS. 1A–1C, a biological agent of interest is entrapped within a matrix 130. The matrix is loaded into channels 110 on the surface of a stent 100, which channels are formed on one or both of the stent abluminal or adluminal surfaces. The matrix allows for release usually sustained release, of the entrapped agent. The stent and matrix is sheathed with a covalently bound gel 140, which may help retain the matrix during transport and implantation of the stent. The stent surface may be derivatized 120 to improve covalent binding.

In one embodiment of the invention, the stent is used to deliver therapeutic agents to a patient, providing the advantage of efficient delivery and sustained release of an agent at a localized site. The system provides the additional advantage of low perturbation at the site of implantation. In another embodiment of the invention, the advantages of the drug delivery system allow for testing and comparison of candidate drugs in an in vivo setting.

Before the present methods are described, it is to be understood that this invention is not limited to particular methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges encompassed within the invention, subject to any specifically excluded limit in the stated range.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a microsphere" includes a plurality of such microspheres and reference to "the stent" includes reference to one or more stents and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Stent.

As used herein, the term stent is used as is known in the art, to refer to a prosthesis which can be inserted and held, when desired, in a lumen of a vessel or organ in the body. Uses include the support of blood vessels, the trachea, renal and urethral tubules, fallopian tubes, eustachian, large and small intestines, etc. Materials commonly used in stent construction include biologically compatible metals, e.g. stainless steel, titanium, tantalum, gold, platinum, copper and the like, as well as alloys of these metals; low shape memory plastic; a shape-memory plastic or alloy, such as nitinol; and the like. Any of these materials can be fabricated to form channels for use in the present invention, and can form, or be derivatized to form, covalent bonds with the matrix.

Non-limiting examples of commercially available stents include the Gianturco-Roubin stent and the Palmaz-Schatz stent, commonly used for tandem short segment stenotic lesions; Wallstent (Boston Scientific, Natick, Mass.), a self expanding stainless stent used for long lesions; Mammotherm stent, Symphony stent, Smart stent, all of self expanding nitinol; the balloon exapandable Perflex, AVE, Intrastent, and Herculink stents, self-expanding Instent, Gianturco Z-stent (Wilson-Cook, Winston-Salem, N.C.), Ultraflex nitinol mesh stent (Microinvasive, Natick, Mass.), and Esophacoil (IntraTherapeutics, Eden Prairie, Minn.). Tracheobronchial stents include the Gianturco Z tracheobronchial tree stent and the Wallstent tracheobronchial endoprosthesis. The stent may be self-expanding, or may be expandable with a balloon, as is known in the art.

Additional platforms for the invention include polymeric biodegradable stents, anastomotic devices, and scaffolds, including synthetic biodegradable or bioerodible porous scaffolds produced using solid free-form fabrication techniques which include selective laser sintering, three-dimensional printing, fused deposition manufacturing, and stereolithography for micro- or nano-fabrication.

Channels.

As shown in FIGS. 1A and 1B, a stent 100 comprises channels 110 on the surface, which may be on either or both of the abluminal (toward the wall) or adluminal (toward the lumen) surfaces. The channels may extend to the end of the stent, forming an open channel, or may be a closed channel. In a preferred embodiment of the invention, the channels are on the adluminal surface and direct delivery to the cells of the vessel wall. Within the channels is a matrix 130 which is covalently bound to the stent surface, which may be derivatized 120 for that purpose.

The dimensions of the channel will be dictated by the requirements for the specific use, and will be sufficient to contain the unit size of the matrix, e.g. microspheres of 1 to 100 µm diameter, and will not be of a depth so great that it compromises the integrity of the stent's structural integrity. The depth will usually be at least about 10 µm, more usually at least about 20 µm, usually not more than about 200 µm, more usually not more than about 100 µm, and preferably are about 45 to 65 µm in depth. The depth is usually greater than about 10% of the total depth of the stent structure, usually greater than about 50% of the total depth of the stent structure, usually not more than about 80% of the total depth of the stent structure.

The length and width of the channel may vary greatly depending on the tissue intended for deployment, for example a cardiovascular stent may have smaller dimensions than an enteral stent. The length of the channel may be up to and including the length of the stent, or where the stent has a strut pattern, along the entire circumference, or a fraction thereof. The width of the channel will be sufficient to contain the unit size of the matrix and still maintain the structural integrity of the stent. For example, the channels are usually at least about 10 µm in width, more usually at least about 20 µm in width, preferably at least about 45 µm in width, where the upper boundary of width is determined by the specific stent design, but is generally not more than about 50 to 75% of the total width of the element, i.e. strut, tube, etc., but could be up to 100% of the width in the case of tapered channels, such as one can get from laser machining the channels.

Channels may be tapered in cross-section, such that the width at the stent surface is wider than the width at the bottom of the channel, e.g. a V shape, a U shape, a V shape with a flat bottom, etc. Where the channel is tapered, at the stent surface, the tapered channel is usually more than about 10% of the strut width, usually more than about 50 or more than about 75% of the surface width, and may be as much as 100% of the surface width. Depth for tapered channels are as described above for a non-tapered channel. The degree of taper will determine the width of the channel at the bottom, where a V-shaped taper will result in a width of about 0 to about 10% of the width of the stent structure. A broader bottom may also find use, where the width of the channel at the bottom will be from about 10% to about 50% of the width of the stent. Channel dimensions and architecture are designed to achieve the desired percent coverage and delivery location while preserving mechanical integrity.

Channels may be fabricated into a stent using known micro- or non-fabrication techniques known in the art, including electro-discharge machining (EDM), laser machining e.g. photolithography, thin-film deposition, wet chemical etching, reactive ion etching, inductively coupled plasma deep silicon etching, laser ablation, air abrasion techniques, injection molding, embossing, and other techniques. Stents may also be comprised of polymeric materials, e.g., plastics, biodegradable polymers, and the like. Such substrates are readily manufactured from microfabricated masters, using well known molding techniques, such as injection molding, embossing or stamping, or by polymerizing the polymeric precursor material within the mold. These polymeric materials may include treated surfaces, e.g., derivatized or coated surfaces, to enhance their utility in the system.

Covalent Attachment.

The gel is covalently bound to the channel surface. The stent surface may be derivatized for covalent binding of a highly viscous agent or component of a gel-forming composition, which can be applied in the absence or presence of channels described above. Where the surface is a metal, it may be first modified with an adhesion agent. The use of silane coupling reagents, especially those of the formula R'Si(OR)$_3$ in which R' is typically an aliphatic group with a terminal amine and R is a lower alkyl or chloro group, to attach a macromolecule or polymer covalently to a solid support is well known in the art. Alkoxy or chloro leaving groups are particularly reactive towards hydroxyl groups found on metal oxide surfaces, where trichlorosilanes are much more reactive than trialkoxysilanes, and appear to form the densest films. Other organosilanes include 3-methacryloxypropyltrimethoxysilane; aminopropyltriethoxysilane (APTES); 3-mercaptopropyltriethoxysilane (MPS); glycidoxypropyltriethoxysilane (GOPS), and the like. In the case of APTES, succinnic anhydride can be used to change the amino functionality to carboxylic acid which is then attached to an amino-linked nucleic acid via carbodiimide coupling. MPS can be used to form disulfide linkages with thiol-containing biomolecules. GOPS has been used in schemes using long polyether chains to provide greater distance and flexibility between the surface and the matrix.

Bifunctional trichlorosilanes have been made so that other molecules can be later attached to the silanized surface. For example, 1-thioacetato-16-(trichlorosilyl)-hexadecane and related analogs have been described as a linking agent for biomolecules. The active silane monomer can also be diluted with a monomer which does not contain the linking group, to effectively "space-out" the active silane monomers that deposit on the surface.

The degree of surface coverage depends on several variables such as reaction time, temperature, degree of hydration of the substrates, nature of the solvent, the cleaning procedure utilized prior to silanization of substrates and the nature/morphology of the oxide layer on the substrate. Methyl terminated diluent silanes provide a hydrophobic alternative to polar materials. Other diluents can be used to provide other functionalities to the surface, for example, the diluent may contain alcohol groups to increase hydrophilicity. The number of carbons in the diluent may also be varied to control the steric environment around the active silane's functional moiety.

Polymer coating of plastic surfaces may be achieved with polyvinyl alcohol, polyethyleneimine, polyacrolein, polyacrylic acid, etc. Direct chemical modification of plastic surfaces includes graft polymerization; halomethylation; plasma deposition of amines, alcohols, and carboxylic acids; nitration followed by reduction; and oxidation.

The linkage may utilize a homo- or heterobifunctional linker having a group at one end capable of forming a stable linkage to the stent surface, and a group at the opposite end capable of forming a stable linkage to the matrix. Illustrative entities include: azidobenzoyl hydrazide, N-[4-(p-azidosalicylamino)butyl]-3'-[2'-pyridyldithio]propionamide), bissulfosuccinimidyl suberate, dimethyladipimidate, disuccinimidyltartrate, N-γ-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl]aminobenzoate, glutaraldehyde, NHS-PEG-MAL; succinimidyl 4-[N-maleimidomethyl] cyclohexane-1-carboxylate; 3-(2-pyridyldithio)propionic acid N-hydroxysuccinimide ester (SPDP) or 4-(N-maleimidomethyl)-cyclohexane-1-carboxylic acid N-hydroxysuccinimide ester (SMCC).

Matrix.

A biodegradable, bioerodible or biocompatible non-biodegradable matrix comprising a biologically active agent is placed within the channels of the stent surface. The matrix may be of any geometry including fibers, sheets, films, microspheres, circular discs, plaques and the like. The size and form of the matrix can be used to control the rate of released period of treatment, and drug concentration. In some situations mixtures of matrices may be utilized employing the same or different biologically active agents. In this way, in a single administration a course of drug treatment may be achieved, where the pattern of release may be greatly varied.

In a preferred embodiment, the matrix is formed to discrete particles, e.g. fibers, spheres, etc., preferably microspheres. Microspheres are usually at least about 5 μm in diameter, more usually at least about 10 μm in diameter, and are usually not more than about 100 μm in diameter, more usually not more than about 50 μm in diameter. Certain drug/microsphere preparations necessitate smaller sizes, e.g. from about 5 μm to about 20μm in diameter due to concentration, molecular charge and volume requirements. In addition, smaller sizes are desirable to ease manual loading or automate loading.

Biodegradable polymers are generally subject to enzymatic or hydrolytic instability. Water soluble polymers may be cross-linked with hydrolytic or biodegradable unstable cross-links to provide useful water insoluble polymers. The degree of stability can be varied widely, depending upon the choice of monomer, whether a homopolymer or copolymer is employed, employing mixtures of polymers, where the polymers may be employed as varying layers or mixed.

Some examples of biodegradable polymers useful in the present invention include: hydroxyaliphatic carboxylic acids, either homo- or copolymers, such as polylactic acid, polyglycolic acid, polylactic glycolic acid; polysaccharides such as cellulose or cellulose derivatives such as ethyl cellulose, cross-linked or uncross-linked sodium carboxymethyl cellulose, sodium carboxymethylcellulose starch, cellulose ethers, cellulose esters such as cellulose acetate, cellulose acetate phthallate, hydroxypropylmethyl cellulose phthallate and calcium alginate, polypropylene, polybutyrates, polycarbonate, acrylate polymers such as polymethacrylates, polyanhydrides, polyvalerates, polycaprolactones such as poly-.epsilon.- caprolactone, polydimethylsiloxane, polyamides, polyvinylpyrollidone, polyvinylalcohol phthallate, waxes such as paraffin wax and white beeswax, natural oils, shellac, zein, or a mixture thereof.

Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate, a slowly eroding polymer is achieved, while erosion is substantially enhanced with the lactate racemate. The matrix may include small amounts of a compound capable of covalently bonding to the stent surface, e.g. including a PEG-dimethacrylate conjugate, or other linkers as described above.

Polysaccharides useful as a matrix include calcium alginate, and functionalized celluloses, particularly carboxymethylcellulose esters characterized by being water insoluble, molecular weight of about 5 kD to 500 kD, etc. Other polymers of interest include polyvinyl alcohol, esters and ethers, which are biocompatible and may be biodegradable or soluble. For the most part, characteristics of the polymers will include biocompatibility, compatibility with the agent of interest, ease of encapsulation, a half-life in the physiological environment of at least 6 hrs; preferably greater than one day, water insoluble, and the like.

Biocompatible, non-biodegradable polymeric compositions are also used as a matrix. Where a non-biodegradable polymer is employed, the rate of release of the drug will be primarily solution/diffusion controlled. The rate of diffusion of drug through the non-biodegradable polymer may be affected by drug solubility, polymer hydrophilicity, extent of polymer cross-linking, expansion of the polymer upon water absorption so as to make the polymer more permeable to the drug, and the like. Diffusion of the drug from the implant may also be controlled by the structure of the implant. The non-biodegradable polymeric compositions employed may be varied according to the compatibility of the polymer with the drug or other active agent to be employed, ease of manufacture, the desired rate of release of the drug, desired density or porosity, and the like. Various non-biodegradable polymers which may be employed are described in U.S. Pat. Nos. 4,303,637; 4,304,765; 4,190,642; 4,186,184; 4,057,619; 4,052,505; 4,281,654; 4,959,217; 4,014,335; 4,668,506; 4,144,317. The non-biodegradable polymers may be homopolymers, copolymers, straight, branched-chain, or cross-linked derivatives.

Biocompatible, non-biodegradable polymers of particular interest include polycarbamates or polyureas, particularly polyurethanes, polymers which may be cross-linked to produce non-biodegradable polymers such as cross-linked poly (vinyl acetate) and the like. Also of particular interest are ethylene-vinyl ester copolymers having ail ester content of 4 to 80% such as ethylene-vinyl acetate (EVA) copolymer, ethylene-vinyl hexanoate copolymer, ethylene-vinyl propionate copolymer, ethylene-vinyl butyrate copolymer, ethylene-vinyl pentantoate copolymer, ethylene-vinyl trimethyl acetate copolymer, ethylene-vinyl diethyl acetate copolymer, ethylene-vinyl 3-methyl butanoate copolymer, ethylene-vinyl 3-3-dimethyl butanoate copolymer, and ethylene-vinyl benzoate copolymer.

Additional naturally occurring or synthetic non-biodegradable polymeric materials include poly(methylmethacrylate), poly(butylmethacrylate), plasticized poly(vinylchloride), plasticized poly(amides), plasticized nylon, plasticized soft nylon, plasticized poly(ethylene terephthalate), natural rubber, silicone, poly(isoprene), poly(isobutylene), poly(butadiene), poly(ethylene), poly(tetrafluoroethylene), poly(vinylidene chloride), poly(acrylonitrile, cross-linked poly(vinylpyrrolidone), poly (trifluorochloroethylene), chlorinated poly(ethylene), poly (4,4'-isopropylidene diphenylene carbonate), vinylidene chloride-acrylonitrile copolymer, vinyl chloride-diethyl fumarate copolymer, silicone, silicone rubbers (especially the medical grade), poly(dimethylsiloxanes), ethylene-propylene rubber, silicone-carbonate copolymers, vinylidene chloride-vinyl chloride copolymer, vinyl chloride-acrylonitrile copolymer, vinylidene chloride-acrylonitrile copolymer, poly(olefins), poly(vinyl-olefins), poly(styrene), poly (halo-olefins), poly(vinyls), poly(acrylate), poly(methacrylate), poly(oxides), poly(esters), poly(amides), and poly(carbonates).

Various techniques known in the art may be employed to entrap the anti-restenotic agent in the matrix. Useful techniques include solvent evaporation methods, phase separation methods, double emulsions methods, UV crosslinking, chemical crosslinking, self-assembling systems based upon covalent or noncovalent interactions, interfacial methods, extrusion methods, molding methods, injection molding methods, heat press methods and the like. The ratio of agent to polymer will vary with the desired rate of release, the amount of agent generally varying in the range of 1 to 80 weight percent of the polymer in addition to other agents present. The ratio of drug to polymer may be adjusted to produce optimized compositions.

Where the matrix is in the form of microcapsules or microparticles, a preformed rate controlling polymer may be dissolved in a volatile substantially water-immiscible solvent, and the agent then added to the polymer-solvent solution. Depending upon the nature of the agent, one may have the agent dispersed in the viscous polymer-solvent mixture or a solid dispersion of drug particles, where the drug will have been pulverized to obtain a fine powder. The matrix may also be formed by mixing the agent with molten polymer at the appropriate temperature, for example for molten polylactic polymer, between 60° to 90° C. The resulting mixture can be cut, molded, injection molded or extruded into any shape or size.

In an alternative method, a coating can be formed around the layered solution to provide an encapsulated matrix for controlled, prolonged release of the active agent. To form the coating, an appropriate aqueous solution, generally water, is slowly poured over the surface. In this manner, polymerization results in a membrane surrounding the drug or agent. Alternatively, the drug and polymer mixture may be extruded to provide, for example, a long rod or fiber. The dispersion or solution can alternatively be added to a rapidly stirred aqueous solution comprising water and a dispersion agent, which may be a protective colloid.

Where desired, the matrix may be formed by one of the methods described above, but in the absence of the active agent. The drug-free matrix may then be loaded with drug by, for example, immersing the matrix in a solution comprising the active agent for a time sufficient for absorption of the drug. Where the activity of the drug will not be compromised, the drug-filled matrix may then be dried or partially dried for storage until use. This method may find particular application where the activity of the drug of choice is sensitive to exposure to solvents, heat or other aspects of the conventional solvent-evaporation, molding, extrusion or other methods.

Gel.

The gel is selected to be a polymeric compound that will fill the spaces between the matrix and the channel, that can be covalently bound to the stent surface and optionally covalently bound to the matrix, and that provides a porous protective barrier between the matrix and the environment, for example during storage, implantation, flow conditions, etc. The gel may contribute to the control of drug release through its characteristics of degradation and diffusion. In additional, the gel may comprise a biologically active agent that is the same or different from the biologically active agent present in the matrix.

Suitable polymers for the gel include poly(methylmethacrylate), poly(butylmethacrylate), plasticized poly(vinylchloride), plasticized poly(amides), plasticized nylon, plasticized soft nylon, plasticized poly(ethylene terephthalate), natural rubber, silicone, poly(isoprene), poly(isobutylene), poly(butadiene), poly(ethylene), poly(tetrafluoroethylene), poly(vinylidene chloride), poly(acrylonitrile, cross-linked poly(vinylpyrrolidone), poly(trifluorochloroethylene), chlorinated poly(ethylene), poly(4,4'-isopropylidene diphenylene carbonate), vinylidene chloride-acrylonitrile copolymer, vinyl chloride-diethyl fumarate copolymer, silicone, silicone rubbers (especially the medical grade), poly(dimethylsiloxanes), ethylene-propylene rubber, silicone-carbonate copolymers, vinylidene chloride-vinyl chloride copolymer, vinyl chloride-acrylonitrile copolymer, vinylidene chloride-acrylonitrile copolymer, poly(olefins), poly(vinyl-olefins), poly(styrene), poly(halo-olefins), poly(vinyls), poly(acrylate), poly(methacrylate), poly(oxides), poly(esters), poly(amides), poly(carbonates), etc., which may be conjugated or combined with other polymers, e.g. PEG, etc. The gel is cross-linked to the stent through the chemistry described above. The polymer may be molded, wrapped, etc. around the stent to provide a protective covering.

Biologically Active Agent.

The biologically active agent delivered to the targeted tissue may be any exogenous agent, particularly agents where it is desirable to achieve a localized concentration, e.g. anti-restenotic agents, anti-tumor agents, etc. Included are pharmacologically active drugs, e.g. antibodies, cytokines, hormones, growth factors, etc.; nucleic acids, e.g. anti-sense oligonucleotides, plasmids, viral genomes, mRNA, etc.; viruses; pro-drugs; pro-drug activators; etc. When drugs are delivered locally via the prosthesis of the invention, they may be at therapeutic levels at the diseased site while at the lower limits of detectability in the bloodstream.

Compounds of interest include chemotherapeutic agents for neoplastic tissues, anti-inflammatory agents for ischemic or inflamed tissues, hormones or hormone antagonists for endocrine tissues, ion channel modifiers for cardiovascular or other tissues, and neuroactive agents for the central nervous system. Exemplary of pharmaceutical agents suitable for this invention are those described in The Pharmacological Basis of Therapeutics, Goodman and Gilman, McGraw-Hill, New York, N.Y., (1993) under the sections: Drugs Acting at Synaptic and Neuroeffector Junctional Sites; Drugs Acting on the Central Nervous System; Autacoids: Drug Therapy of Inflammation; Water, Salts and Ions; Drugs Affecting Renal Function and Electrolyte Metabolism; Cardiovascular Drugs; Drugs Affecting Gastrointestinal Function; Drugs Affecting Uterine Motility; Chemotherapy of Parasitic Infections; Chemotherapy of Microbial Diseases; Chemotherapy of Neoplastic Diseases; Drugs Used for Immunosuppression; Drugs Acting on Blood-Forming organs; Hormones and Hormone Antagonists; Vitamins, Dermatology; and Toxicology, all incorporated herein by reference. Agents may be in the form of simple drugs, peptides, peptide fragments, DNA, RNA, ribozymes or engineered hybrids of nucleic acids and peptides or peptide fragments, or derivatives of each.

The method of the invention can be exploited as a platform for delivery of genetic materials and thus is useful in a variety of applications. Nucleic acids that correct genetic deficiencies can be introduced into a targeted tissue, e.g. blood vessels, intestines, etc.

Specific agents of interest include therapeutic agents that inhibit in-stent restenosis. Such agents may include rapamycin; antiplatelet agents; GPIIb/IIIa inhibitors, e.g. RheoPro; DNA; ribozymes; RNA; antiplatelet drugs, e.g.

aspirin and dipyridamole; anticoagulant drugs, including heparin, coumadin, protamine, and hirudin; antimitotics (cytotoxic agents) that work directly to prevent cell mitosis (replication) and antimetabolites that prevent replication, e.g. methotrexate, colchicine, azathioprine, vincristine, vinblastine, fluorouracil, adriamycin, mutamycin, etc. Anti-inflammatory drugs such as glucocorticoids, e.g. dexamethasone, betamethasone, etc. can also be useful to locally suppress inflammation caused by injury to luminal tissue during angioplasty.

Angiotensin converting enzyme inhibitors (ACE-I) are used for antihypertensive and renoprotective actions. ACE inhibitor include, but are not limited to, captopril, benazepril, enalapril, fosinopril, lisinopril, quinapril, Ramipril, imidapril, perindopril, erbumine, and trandolapril. ACE receptor blockers may also be used in place of or as well as ACE inhibitors, and these include losartan, irbesartan, candesartan, cilexetil, and valsartan.

Nicotine receptor agonist, e.g. nicotine (S-3-(1-methyl-2-pyrrolidinyl)pyridine) and other compounds that substantially specifically bind a nicotine receptor and provide a pharmacological effect. "Nicotine receptor agonists" encompass naturally-occurring compounds (including, but not limited to, small molecules, polypeptides, peptides, etc., particularly naturally-occurring plant alkaloids, and the like), endogenous ligands (e.g., purified from a natural source, recombinantly produced, or synthetic, and further including derivatives and variants of such endogenous ligands), and synthetically produced compounds (e.g., small molecules, peptides, etc.) The term "nicotine" further includes any pharmacologically acceptable derivative or metabolite of nicotine which exhibits pharmacotherapeutic properties similar to nicotine. Such derivatives, metabolites, and derivatives of metabolites are known in the art, and include, but are not necessarily limited to, cotinine, norcotinine, nornicotine, nicotine N-oxide, cotinine N-oxide, 3-hydroxycotinine and 5-hydroxycotinine or pharmaceutically acceptable salts thereof.

Agents that increase nitric oxide are of interest as anti-restonic agents, e.g. S-nitrosopenicillamine, sodium nitroprusside, N-ethyl-2-(1-ethyl-2-hydroxy-2-nitrosohydrazino) ethanamine (NOC 12), etc. The production of nitric oxide may also be modulated by cytokines, such as γ-interferon, tumor necrosis factor, IL-1, IL-2 and endotoxin due to their effect on the enzyme, nitric oxide synthase. The inducible form of NO synthase is increased by cytokines and the constitutive form seems to be decreased by cytokines. HMG-CoA reductase inhibitors have been found to upregulate endothelial cell NOS activity, as described by U.S. Pat. No. 6,147,109, Liao et al. Any of the forms of nitric oxide synthase can be utilized, as the protein or an active fragment derived therefrom, or as a DNA construct for expression.

Also of interest for the inhibition of restenosis are compounds with an anti-angiogenic effect. These include the anti-angiogenic polypeptides: angiostatin (O'Reilly et al (1994) Cell 79:315–328); endostatin (O'Reilly et al. (1997) Cell 88: 277–285); and anti-angiogenic anti-thrombin III (Bock et al. (1982) Nucleic Acids Res. 10 (24), 8113–8125); and the like, and further include functionally active variants and derivatives thereof. Other anti-angiogenic agents include inhibitors of matrix metalloproteases, e.g. amifostine, WR-1065; marimastat, primomastat, alpha-1 antitrypsin; and the like.

Alternatively, compounds that block thrombin, and other anti-coagulants, may be used to inhibit restenosis, such compounds based on the tripeptide motif D-Phe-Pro-Arg; e.g. LY287045, etc. Many compounds, such as inogatran and melagatran, are known in the art. For non-limiting examples, see U.S. Pat. Nos. 6,326,386; 6,232,315; 6,201,006; 6,174,855; 6,060,451; and 5,985,833; among others.

Agonists of the TGF-beta receptor are also of interest. TGF-β receptor Type I and type II mediate most activities of TGF-beta (Ebner et al. (1993) Science 260:1344–1348; and Franzen et al. (1993) Cell 75: 681–692). Ligands include TGF-β, and mimetics and biologically active derivatives thereof.

For the induction of apoptosis, agents of interest include death domain receptor ligands, which are compounds, usually polypeptide compounds, that bind to mammalian cell surface receptors comprising a death domain, or homologs or orthologs thereof, and that, by binding so deliver a signal for apoptosis to the cell. The intracellular protein interactions triggered by these receptors can be attributed to binding interactions of the death domain, which is homologous to an approximately 80 amino acid domain near the C-terminus of TNF-R1, and is responsible for signaling cytotoxicity (Huang et al. (1996) Nature 384:372–5). The TNF receptor death domain family includes TNF-R1, Fas (CD95), TRAMP (wsl/Apo-3/DR-3), TRAIL-R1 (DR-4) and TRAIL-R2 (DR-5, TRICK2, KILLER). Death domain ligands include proteins that regulate cellular proliferation and differentiation by binding to specific death domain receptors. These ligands include the TNF family, e.g. TNF, lymphotoxin, CD30 ligand, 4–1 BB ligand, CD40 ligand, CD27 ligand, and TRAIL (TNF-related apoptosis-inducing ligand), and homologs and analogs thereof. The functional, soluble forms of TNF as well as human FasL exists as trimers. Lymphotoxin β, a member of the TNF family, consists of a heterotrimer of one (lymphotoxin-α, or TNF-β) and two β chains (lymphotoxin-β) on the membrane.

Anti-restenotic polypeptides and peptides can be administered in their native form, or through the administration of nucleic acids encoding the molecule of interest. Administration of nucleic acids results in genetic alteration of targeted cells. The nucleic acid materials for delivery to targeted tissue encodes a gene product for which expression is desired, and a promoter for expression of the gene product. By "nucleic acid of interest" is meant any DNA, RNA, ribozyme, hybrid or analog thereof that encodes a polypeptide or other gene product that is desirable for expression in tissue of a subject. The gene product can include a polypeptide, an anti-sense mRNA, or other gene product that is desirably expressed. The term "DNA of interest" or "DNA" is used herein as shorthand to refer to the nucleic acid of interest and is not meant to be limiting. The nucleic acid delivered to the tissue in vivo can take any number of forms. For example, the nucleic acid can be introduced as a linear or circular molecule, preferably a circular molecule (e.g., a circular plasmid or other construct).

The nucleic acid of interest and the promoter are operably linked to provide a construct, or vector for expression. Normally, "construct" will refer to a nucleic acid molecule that facilitates expression of a gene product encoded by the nucleic acid to be introduced. By "operably linked" is meant that a DNA sequence and a regulatory sequence(s) (e.g., a promoter sequence) are connected in such a way as to permit transcription when the appropriate molecules (e.g., transcriptional activator proteins) are bound to the regulatory sequence(s).

The amount of DNA to accomplish expression of an anti-restenotic gene product at an effective level will vary according to the desired effect, as well as with other variables such as the age of the subject, the tissue to be genetically altered, the gene product to be expressed and the desired level of its expression, etc. In general, the amount of DNA administered is an amount sufficient to provide for transformation of a number of cells that in turn provides for a level of gene product expression from the introduced DNA to provide for a desired effect. Dosages are routinely determined in the art, and can be extrapolated from the amounts of DNA effective in an animal mode (e.g., a rodent (mouse or rat) or other mammalian animal model), in which factors such as the efficiency of transformation and the levels of gene product expression achieved can be readily assessed and extrapolated to other vertebrate subjects.

The nucleic acid of interest can be obtained from any of a variety of sources or methods well known in the art, e.g. isolated from suitable cells, produced using synthetic techniques, etc., and the constructs prepared using recombinant techniques well known in the art. Likewise, techniques for obtaining expression of DNA or RNA sequences in a genetically altered host cell are known in the art (see, for example, Kormal et al., Proc. Natl. Acad. Sci. USA, 84:2150–2154, 1987; Sambrook et al. Molecular Cloning: A Laboratory Manual, 2nd Ed., 1989, Cold Spring Harbor Laboratory Press, Cold Spring Harbor, N.Y.; each of which are hereby incorporated by reference with respect to methods and compositions for eukaryotic expression of a DNA of interest).

Expression of the introduced nucleic acid can be short-term, i.e. a few hours to several hours to a few days, or permanent or long-term i.e. from a week to several weeks to a few months or more. In general, gene product expression from the introduced nucleic acid ranges from at least about 1 to 2 days, or 3 to 5 days, to about 1 week, generally about 1 to 4 weeks, up to about 6 weeks, and may be as long as about 10 to 12 weeks or longer. Where expression times of more than a few weeks are desired, for example from about 10 to 12 weeks or longer, expression of the gene product can be maintained by using a retroviral construct having inactivated LTRs and an internal promoter in the construct to drive gene product expression.

Complex systems of drugs may be carried by the prosthesis. An anticoagulant or antiplatelet may be included in the outermost surface of the device in order to elute off very quickly for the first several days. Antiinflammatories and antireplicates can be formulated into the device to continue to elute later, when in contact with non-blood cells after neointima overgrowth has surrounded the device. The drug elution rate does not need to be uniform, and may be tailored to fit the need of the patient.

Methods of Use

Therapeutic Uses.

The drug delivery system of the present invention is useful for any vascular surgery, such as may be used in any situation in which the flow of blood through a vessel has been compromised. There are a variety of conditions where there is restricted blood flow through that vessel. Occlusive vascular conditions of interest include atherosclerosis, graft coronary vascular disease after transplantation, vein graft stenosis, peri-anastomatic prosthetic graft stenosis, restenosis after angioplasty, coronary artery disease, peripheral vascular disease or other forms of occlusive arterial disease, and the like.

In a complex biological process such as restenosis, a therapeutic strategy may involve multiple therapeutic factors, e.g. released with multiple time courses. Strategies may utilize combinations of microspheres and gels containing different agents and/or that are formulated for different release profiles. Due to their versatility, the controlled release materials can be adapted and combined to provide the desired time course and dose-response for each stent and application.

Other uses include conditions affecting the gastrointestinal tract. Malignant obstruction of the stomach, esophagus, or duodenum causes nausea, vomiting, esophagitis, electrolyte imbalance, poor nutrition, and severe dehydration. Causes include primary tumors of the stomach and duodenum, malignant infiltration by neoplasms from adjacent organs (e.g., pancreas), and compression by malignant regional lymphadenopathy. Expandable stents offer a non-surgical alternative for treatment. These are particularly useful in poor surgical candidates with malignant obstruction of the gastric outlet. The ability to treat duodenal obstruction secondary to extrinsic compression from pancreatic cancer further expands the spectrum of indications of stent placement for primary nonsurgical palliation. Stents have also been used in patients with benign gastroduodenal strictures when conventional surgical resection or bypass was not possible or wanted. In patients with benign disease, coexistent morbid factors involving the cardiopulmonary systems may limit surgical options, which makes the use of metallic stents more attractive. In all cases, the ability to provide therapeutic agents in addition to the stent provides enhanced benefits.

Other vessels of the body may be repaired with a stent, including the trachea for breathing disorders, renal and urethral tubules, fallopian tubes for the treatment of infertility, eustachian tubes for the treatment of chronic ear infection and other hearing disorders, etc. Biologically active agents of interest include those described above.

Drug Evaluation.

The drug delivery platform of the present invention finds use in the evaluation of drug candidates, for example to test efficacy in preventing in-stent restenosis. A test sample comprising a candidate drug is entrapped within a matrix, and used in the drug delivery platform as described above. The stent is then implanted in a biologically relevant model, e.g. an animal model of injury after balloon angioplasty, and the effect on the condition of interest evaluated after a period of time sufficient to observe an effect. The results may be compared to various controls, including stents lacking pharmacologic agents; stents comprising an agent with known efficacy; combinations of matrix polymers, combinations of gel polymers, variations in stent design, and the like. The results can be entered into a data processor for reference, and algorithms used for the comparison and analysis of results obtained under different conditions. Mathematical systems can be used to provide quantitative measures of similarities and differences between results. For example, the translation profiles in the database can be analyzed by pattern recognition algorithms or clustering methods, e.g. hierarchical or k-means clustering, etc., that use statistical analysis to quantify relatedness. These methods can be modified by weighting, employing classification strategies, etc. to optimize the ability of a translation profile to discriminate different functional effects.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Kits

Contemplated in the invention is kits for the use of the drug delivery platform in clinical use or in compound testing. Kits will comprise at least a channeled stent, which may be derivatized for covalent bonding of the gel; and polymers for the matrix and gel. The components may be previously assembled, including a biologically active agent of interest; or may be provided in component form for addition of an agent of interest. Such kits may further comprise packaging, e.g. to prevent damage during shipping; and instructions for use. Kits for compound testing may further comprise agents of known activity for use as controls, and the like.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXPERIMENTAL

EXAMPLE 1

Stent-based Local Delivery Platform

Stent Design and Loading.

The stent design for this initial example is based on the Palmaz-Schatz coronary stent. The stainless steel stent is 1.6 mm in diameter and 10 mm in length and has 10 longitudinal struts evenly spaced circumferentially, and it is designed to be balloon expandable up to 5 mm diameter. Its basic slotted tube design was modified by electro-discharge machining (EDM) channels 80 microns wide by 60 microns deep along the length of the abluminal (toward the wall) side of each strut. The stent is designed to provide abluminal (toward the wall) but not adluminal (toward the lumen) delivery. With these dimensions, the channels cover 8.5% of the lumen wall area when deployed to a nominal diameter of 3 mm. The channels were machined from end to end in order to allow drug delivery both to the wall and to the tissue surrounding the stent end which both represent critical sights for neointima formation. Microspheres, which can hold and release therapeutic agents (for example, see Yuksel et al. (2000) *Plast Reconstr Surg.* 105(5):1721–9; Waugh et al. (1999) *Circ Res.* 84(1):84–92 were mechanically loaded into these channels. Excess microspheres were removed with a needle and short bursts of air from a compressed air canister.

The corresponding design and post-manufacture stent appear as FIGS. 1A to 1C. No mechanical failures occurred during the deployment of over 60 stents of this design. Stent channels were filled by manual loading with PLGA (75:25)-PEG-buffer microspheres with a mean diameter of 50 µm. Predetermination of microsphere size can be difficult for certain drug-loads, and smaller microspheres are more readily loaded. As a result, quantitative evaluation of stent filling as percent of total channel was subsequently evaluated for both large and small microspheres.

Microsphere Preparation.

Bioerodible polyethylene glycol-polylactide-co-glycolide (PLGA, Polysciences, Warrington, Pa.) microspheres (MS) were prepared as a modification of previously described techniques (Yuksel, et al, supra.) A mixture of 8:1:PLGA (75:25):PEG-8000 (polyethylene glycol, MW 8000, Sigma, St Louis, Mo.) was employed with the double emulsion technique to generate microspheres (MS) of final diameter 50 or 10 µm. Additionally, a pH buffer of 7.4 was incorporated in all MS preparations as a modification of other techniques to limit local pH changes (Zhu et al (2000) *Nature Biotechnology* 18:52–7. Separately, MS containing PEG-dimethacrylate instead of PEG were also prepared to a final size of 10 µm.

In Vitro Flow Retention and Channel Fill Density Determination.

To evaluate whether flow over the surface of the loaded stents resulted in dislodging of MS, stents were advanced into in vitro flow. Loaded MS-stents were mounted on a 4.0 mm x 2.0 cm noncompliant balloon. Two 25–30 cm segments of Tygon tubing were joined with a 5 cm segment of shrink tubing. Phosphate buffered saline (PBS) was introduced and adjusted to a flow rate of 250 ml/min. The stent was introduced from the downstream end of the tubing and advanced to the center of the shrink-tubing segment and maintained for a total of 2.0 minutes. The stent was withdrawn and employed for fill density analysis.

To determine the mean percent of each channel that was filled with MS, the entire length of each channel was photographed with single composite photographs of each generated and employed in ImagePro Image analysis suite. Stents were examined on a Nikon E600 microscope with plan apochromat lenses at a total magnification of 40X. High resolution digital images were acquired using a Diagnostic Instruments true color SPOT camera. The entire length of each channel was photographed with single composite photographs of each generated and employed in ImagePro image analysis suite to determine the mean percent of total channel filled with MS.

Figure 2:
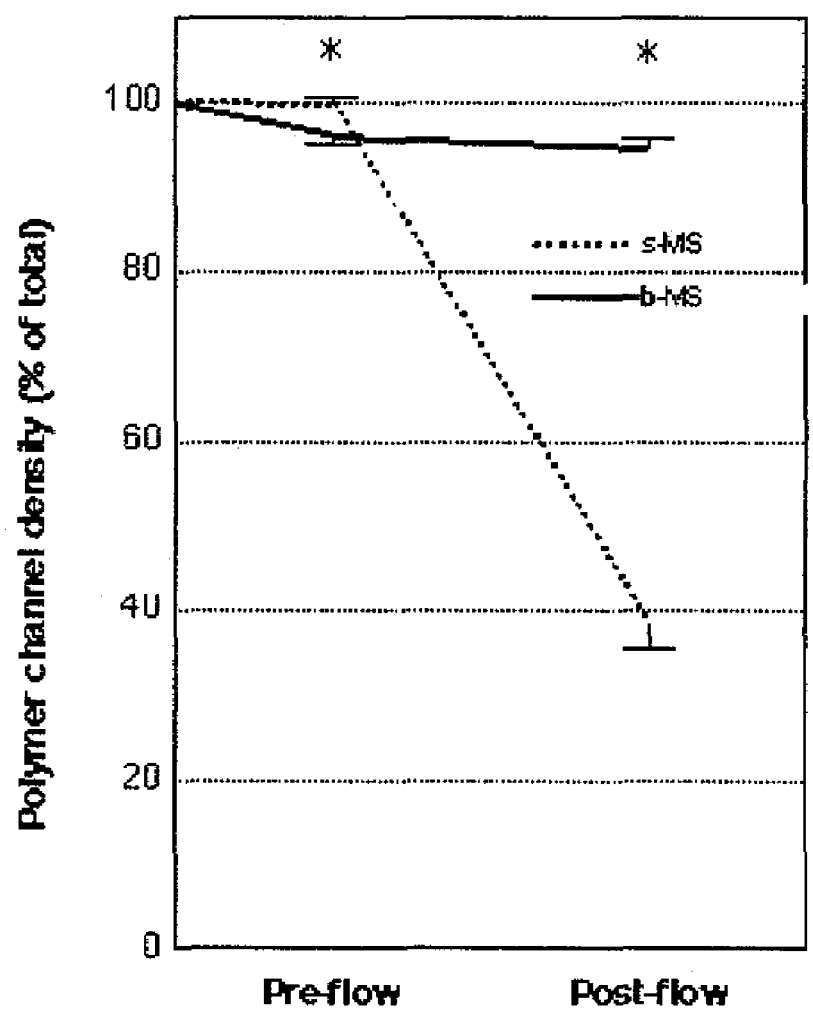
FIG. 2 is a graph depicting size-dependent flow retention. Microspheres of 50 µm (b-MS) or 10 µm (s-MS) were loaded onto a stent to complete fill density, then balloon mounted and subjected to in vitro flow with channel fill density recalculated after each step. The mean channel density (±SE) for b-MS (solid line) and s-MS (dotted line) is shown before and after flow exposure, "*" denotes $P<0.05$.

Stents were manually loaded with microspheres of mean diameter 50 µm (b-MS) or 10 µm (s-MS), loaded onto a balloon, and the entire length of each stent channel was photographed. Mean channel fill density was calculated as the percent of total channel filled with microspheres. Stents were subsequently introduced into a flow loop in vitro in a transparent segment of tubing. The entire length of each stent channel was again photographed and analyzed. Results of both analyses are summarized as FIG. 2. No statistically significant decrease in b-MS loading occurred after introduction to flow (P=0.3351), while s-MS encountered significant loss of microspheres in flow conditions (P=0.0001). However, certain drug/microsphere preparations necessitate smaller sizes due to concentration, molecular charge and volume requirements. In addition, smaller sizes are desirable to ease manual loading or automate loading. Given that some drug loads may necessitate small final MS sizes and small MS offer some technical advantages for stent-loading, strategies for hybrid systems to increase s-MS retention were subsequently investigated.

Hybrid Strategies for Retention In Vitro and In Vivo-Gel Preparation and Stent Loading.

Stents were either rinsed with saline or pretreated with 2% 3-methacryloxypropyltrimethoxysilane (meac) in 75% ethanol and heat cured for 60 minutes at 105° C. (silane-stents employed where described). The s-MS (either meac-MS or MS) were loaded as before and loaded stents were ensheathed in silicone tubing. One set of stents was loaded with 30% pluronic F-127 at a temperature of 4° C. For other groups, a 20% mixture of 3:2:PEG-dimethacrylate:PEG with 900 ppm photoinitiator (HMPP) was introduced to fill unoccupied spaces within the channels. Ensheathed stents were exposed to UV-A overnight. Silicone tubing was withdrawn. Stents were loaded on 4.0 mm×2.0 cm noncompliant balloons and lyophilized overnight prior to use.

To evaluate whether in vivo advancement and deployment altered MS density, adult male New Zealand White rabbits weighing 3.8–4.2 kg underwent general anesthesia induced with ketamine/medetomidine and maintained with isoflurane. An arteriotomy was performed and a 5F introduction sheath was placed. Under fluoroscopic guidance using a Siemans Angiostar, aseptically prepared stents were deployed in the infra-renal abdominal aorta. Pre- and post-deployment digital subtraction angiograms were recorded for each. Stents were post-dilated with a 5 mm angioplasty balloon (Jupiter, Cordis, Miami, Fla.) to a final lumen size of 125% of baseline with care taken to ensure that no branches were present within 5mm of either end or within the stent segment. Post-deployment angiograms were also recorded for each. Animals employed for channel fill density analysis underwent total-body perfusion-fixation under anesthesia with immediate excision of the aortic segment containing the stent. Stents were photographed for channel fill density as above both through the aortic wall and after excision from the aortic segment. Animals undergoing plaque evaluation and inflammatory infiltrate analyses were recovered and maintained for 7 days prior to total-body perfusion fixation as previously described. Treated segments were harvested, stents carefully excised and segments postfixed in neutral buffered formalin (NBF) for 12–14 hrs. Specimens were paraffin embedded and employed for plaque analysis or evaluation of local inflammatory infiltrate as described.

Figure 3:
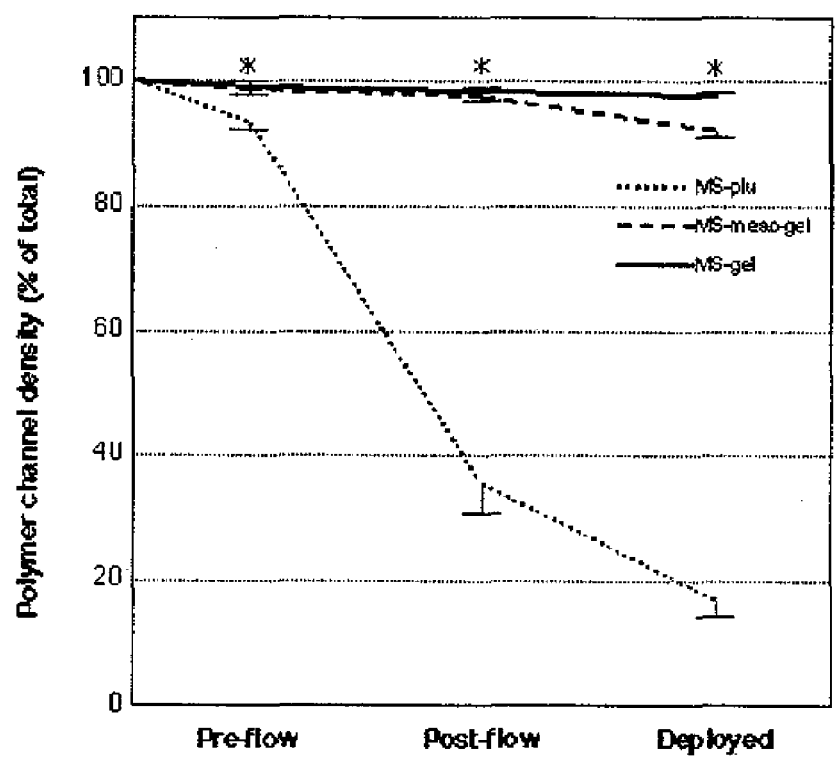
FIG. 3 is a graph depicting hybrid retention in vitro and in vivo. Microspheres of 10 µm were loaded onto a stent to complete fill density, and combined with pluronic gel (MS-plu), stent-anchored PEG-methacrylate gel (MS-gel) or stent- and MS-anchored PEG-methacrylate gel (MS-meac-gel). The mean channel density (±SE) for MS-plu (dotted line), MS-gel (solid line), and MS-meac-gel (dashed line) is shown after balloon loading, in vitro flow exposure or in vivo deployment in rabbit aorta, "*" denotes $P<0.05$.

Stents containing s-MS were again prepared as above and ensheathed en toto in silicone tubing. The spaces around the MS within each channel were filled with a rapid-release gel formulation in an attempt to prevent loss of s-MS under flow conditions. The entire length of each stent channel was again photographed and mean channel fill density calculated. These stents (MS/plu) were subsequently introduced into an in vitro flow loop, and channel fill density was calculated after flow exposure. Finally, MS/plu stents were introduced into the rabbit common femoral artery, advanced and deployed in the infrarenal abdominal aorta. The aortic segments were subsequently excised and mean channel fill density after in vivo deployment was calculated both through the nearly transparent aortic wall (results not depicted) and after stent removal. Stent removal did not result in significant change in fill density. As depicted in FIG. 3, gel loading results in minimal loss of fill density, but exposure to flow again results in substantial loss of s-MS from the stent ($P=0.0001$). In vivo deployment encounters still worse retention rates ($P=0.0201$).

Figure 4:
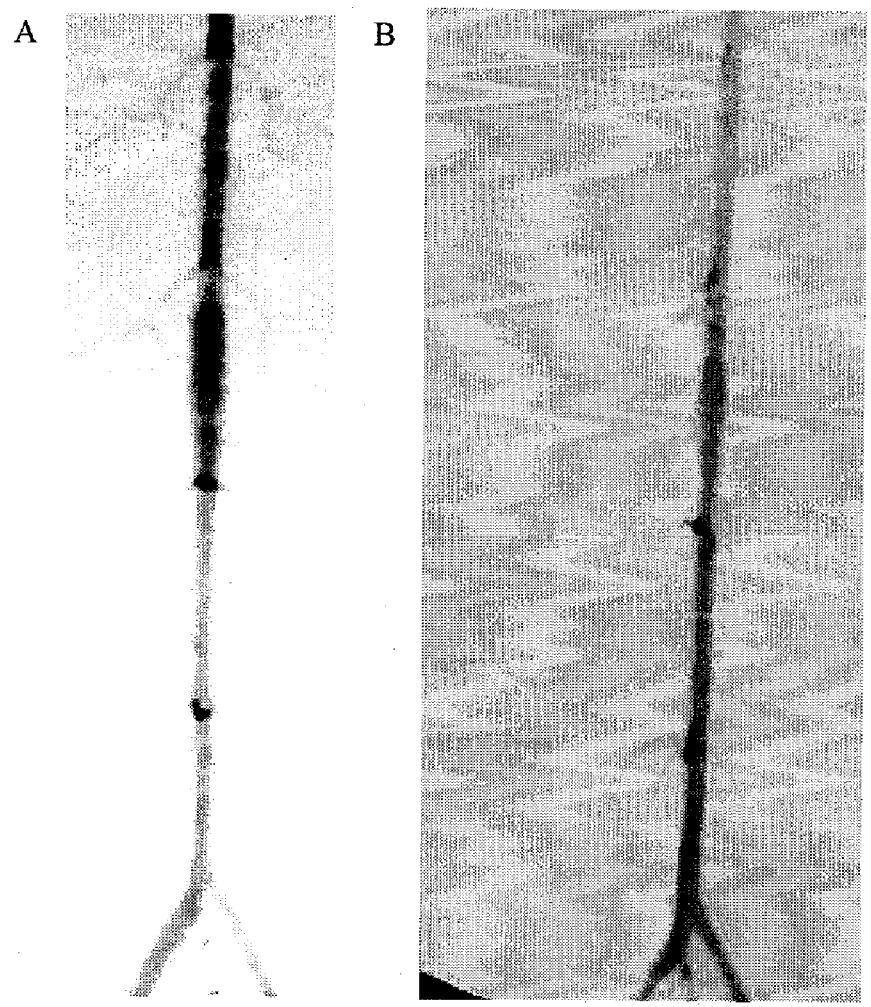
FIGS. 4A and 4B are representative digital subtraction angiograms after in vivo MS-gel deployment. No immediate post-deployment (FIG. 4A) or late (pre-harvest, FIG. 4B) mechanical failures or complications are present.

New stents were pretreated to form a metal oxide-methoxysilane-monomethacrylate link to the metal-oxide layer of the stent surface. Silane stents were then loaded with either s-MS containing PEG-dimethacrylate or s-MS with PEG as above. Stents were ensheathed and a 20% mixture of 3:2: PEG-dimethacrylate:PEG was introduced to fill unoccupied spaces within the channels. Gels were subsequently polymerized to form gel-stent links (MS-gel) or gel-stent-microsphere links (MS-meac-gel). Stent channel fill density was again evaluated after balloon loading, after in vitro flow loop exposure and after in vivo deployment in rabbit aortas. Significant improvements in s-MS retention occurred for MS-gel in vivo relative to MS-plu ($P=0.0001$) and in vitro under flow conditions ($P=0.0001$ vs. MS-plu, $P=0.0001$ vs. s-MS). Most importantly, no significant loss occurred when MS-gel groups were subjected to flow conditions ($P=0.3336$) or in vivo deployment ($P=0.4244$). While MS-meac-gel had statistically significant improvements in MS retention in vitro and in vivo relative to MS-plu ($P=0.0010$, $P=0.0001$ respectively) and s-MS ($P=0.0001$ in vitro), these meac-s-MS particles were far less efficiently loaded than with s-MS without methacrylate. Additionally, MS-meac-gel exhibited significant loss of MS after in vivo deployment ($P=0.0004$) while MS-gel did not. Thus, MS-gel exhibited the best performance under all conditions. Additionally, no mechanical failures (fractures, perforations, etc.) or complications occurred in any group, including MS-gel. As depicted in the representative digital subtraction angiogram of MS-gel stent (FIG. 4), immediately post-deployment (panel a) there is distal spasm but no luminal compromise, perforation, or failure. By the time of harvest, the lumen remains patent, the stent intact, and no complications are present, as depicted in panel 4b.

In summary, a solution for hybrid MS-retention is a gel that protects the microspheres from embolization during advancement and deployment. A crosslinked PEG-methacrylate gel was subsequently investigated. Initial experiments revealed that channel contents separated from the stent readily but did not fragment from one another. The stent channels were subsequently modified to add a methacrylate link to the metal-oxide layer of the stent in order to enhance channel retention of the polymers. Small microspheres were either prepared as before or modified to contain PEG-methacrylate. Gel polymerization thus anchored the gel to the channel and, in the latter group, to the surface of the microspheres themselves. Retention rates for this gel system were virtually complete under flow and after in vivo deployment. Thus, a stent system potentially allowing controlled drug delivery without embolization of polymers was developed. Given the progressive loss of methacrylate MS when exposed to flow and in vivo deployment and the relative ease of loading s-MS without methacrylate, subsequent experiments incorporated s-MS without methacrylate.

Local Inflammation.

To evaluate whether the stent platform altered local inflammatory infiltrate, paired sections from the 7 day timepoint above were employed for granulocyte determination using chloroacetate esterase staining or for macrophage evaluation using immunohistochemistry (RAM-11, DAKO, Carpinteria, Calif.) as previously described by Waugh, et al. (2000). *Circulation* 102:332–337. Number of granulocytes and macrophages was determined for each cross section, with mean and standard error tabulated by group.

Since certain polymer systems have been shown to lead to local inflammation, cross-sectional macrophage and neutrophil infiltrate were examined for each group. Results are detailed in Table 1. No statistically significant differences in local macrophage or neutrophil infiltration occurred in MS-gel vs. Palmaz-Schatz stents (P-S) ($P>0.05$ for each comparison).

TABLE 1

Inflammation after stent implantation in vivo.

| | Neutrophilic Granulocytes | Macrophages |
|---|---|---|
| P-S | 96.1 ± 8.9 | 0.267 ± 0.153 |
| MS-gel | 90.0 ± 8.8 | 0.133 ± 0.091 |

Number of granulocyte esterase positive (neutrophilic granulocytes) or RAM-11 positive (macrophages) cells per cross section (mean ± SE).

Plaque Evaluation.

To evaluate whether the stent platform itself worsened plaque formation and whether the system could detect any therapeutic effect, animals (n=5 per group) underwent stent implantation with normal (unchanneled) commercially available Palmaz-Schatz stents of identical dimensions, channel stents containing s-MS/PEG gel as prepared above (without any therapeutic factor), or channel stents loaded with s-MS/PEG gel containing a nitric oxide donor as an antineointimal agent. The NO-nucleophile complex in this study, N-Ethyl-2-(1-ethyl-2-hydroxy-2-nitrosohydrazino) ethanamine (NOC-12, Calbiochem, San Diego, Calif.), releases two equivalents of NO per NOC-12. Animals were recovered and maintained on 0.25% cholesterol chow. On day 7, treated segments were excised and processed as described and cross sections employed for Verhoff elastica-Masson trichrome double staining as previously described (Waugh et al., supra.) Photographs of each aorta were acquired as before. Ratio of intima to media for each cross section was determined from the appropriate area measurements, with mean and standard error tabulated for each group.

Figure 5:
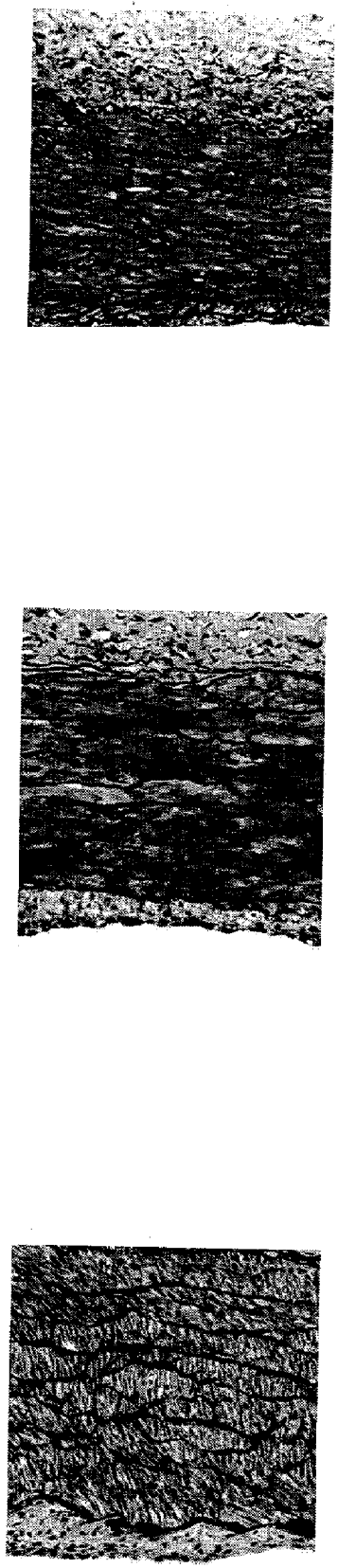
FIGS. 5A, 5B and 5C are photographs depicting early in-stent plaque formation. Representative photos were taken at midpoint between stent struts for rabbit aortas 7 days after deployment of (5A) Palmaz-Schatz stent (P-S), (5B) stent containing microspheres and anchored PEG-methacrylate gel (MS-gel), or (5C) MS-gel platform containing a nitric oxide donor as a therapeutic anti-restenotic agent (MS-gel-tx).

The impact of MS-gel stents on in-stent restenosis was subsequently evaluated, along with the suitability of this system to evaluate anti-restenotic agents. Briefly, animals underwent implantation of normal P-S stents, MS-gel stents containing polymer only (MS-gel), or MS-gel stents containing a therapeutic level of a nitric oxide donor as an anti-restenotic agent (MS-gel-NO). Early plaque formation was evaluated after 7 days through intima to media ratios to evaluate whether stent design or therapeutic factor altered early in-stent restenosis in a critical window. The results are summarized in FIG. 5. As indicated, MS-gel stents did not encounter significantly altered rates of early in-stent restenosis relative to P-S controls (P=0.1126). In contrast, MS-gel-NO stents reveal a significant reduction in early plaque reduction relative to both controls (P=0.0001 vs. P-S, and P=0.000vs. MS-gel).

Given that polymer systems prepared differently than those employed here have encountered high rates of inflammation and may adversely impact plaque formation, in vivo deployment of this stent system was evaluated relative to deployment of commercially available Palmaz-Schatz stents. The polymer-loaded stents encountered comparable rates of local macrophage and neutrophilic granulocyte infiltration after seven days relative to Palmaz-Schatz stents as detailed above. Perhaps more importantly, no statistically significant alteration in rates of in-stent plaque formation was evident relative to conventional stents of comparable dimensions. Thus, these polymer-loaded stents do not appreciably worsen the system which they were designed to evaluate and treat. These results are in sharp contrast to recent reports of polymer-only systems which require cytotoxic agents to avert increases in inflammation and plaque progression relative to conventional stents (Tamai et al. (2000) *Circulation* 102:399–404; van der Giessen et al (1996) *Circulation* 94:1690–1697; Colombo and Karvouni (2000) *Circulation* 102(4):371). Given the technical, mechanical and biologic disadvantages of alternative local release strategies, no prior evaluation of potential anti-restenotic local agents has been effectively undertaken. The present platform thus represents an important and necessary step in the development of effective strategies for in-stent restenosis and management of cardiovascular disease.

We subsequently evaluated whether the present system was sensitive enough to detect therapeutic levels of an anti-restenotic agent of any nature. Here, in vivo deployment of this system with one such agent, a nitric oxide donor, resulted in substantial declines in plaque formation relative to both polymer-loaded stent controls and conventional Palmaz-Schatz stents alone. Thus, this system has proven to be a relatively nonperturbing, effective, and sensitive method for evaluation and therapeutic delivery of putative anti-restenotic agents. Previously, identification of drugs locally effective in preventing in-stent restenosis has proven difficult, due to lack of a simple controlled release platform.

With the present platform, selection and optimization of agents to locally prevent in-stent restenosis can now be readily accomplished. Although demonstrated here in a variation of a Palmaz-Schatz stent for simplicity, the present strategy can be translated to virtually any stent design type.

Alternative Stent Designs.

The strategies for local drug delivery described above are applied to other mechanical stent designs and can be accomplished with other machining techniques. For example, using laser machining techniques similar to those currently employed to manufacture modern stents, channels were cut into the abluminal surface of a BX-Velocity stent (Cordis Corporation, Miami, Fla.). The channels shown are approximately 75 microns in width and 60 microns deep and follow the strut pattern faithfully around the entire stent circumference. Channeled BX-Velocity stents have been treated successfully with the s-MS/PEG gel preparation.

EXAMPLE 2

Stent-based Release of an Angiogenesis Inhibitor Limits In-stent Plaque Progression Microsphere Preparation.

Biodegradable poly(lactic-co-glycolic-acid)-polyethylene glycol (PLGA/PEG) microspheres were prepared as a modification of previously described techniques. A mixture of 8:1:PLGA(75:25):PEG-8000 was employed with the double emulsion technique to generate a final microsphere diameter of 10 microns, and a degradation time of approximately 4 weeks. Additionally, a pH buffer of 7.4 was incorporated to limit local pH changes in order to stabilize incorporated drugs and render the microspheres more biocompatible. During the microsphere manufacturing process, 2.0 mg of the angiogenesis inhibitor angiostatin (Calbiochem, La Jolla, Calif.) in 200 ml phosphate buffered saline was added to the polymer solution. Control microspheres (blank microspheres) containing polymer and buffer without any drug were also prepared. Stents were prepared as above.

In Vivo Stent Implantation.

Age-matched adult male New Zealand White rabbits weighing 3.8–4.2 kg were used in accordance to NIH and institutional guidelines (n=6 animals per group). Under general anesthesia, an arteriotomy at the femoral artery was performed and a 5 Fr introducing sheath was placed. Under fluoroscopic guidance, aseptically prepared channeled stents filled with blank or angiostatin microspheres were deployed in the infra-renal abdominal aorta. Stents were post-dilated at 8 atm with a 5 mm angioplasty balloon (Jupiter, Cordis, Miami, Fla.) to a final lumen size of 125% above the baseline with care taken to ensure that angiostatin branches were present within the stent segment. Pre- and post-deployment digital subtraction angiograms were recorded for the blank procedural control and angiostatin treatment groups. The rabbits were fed a 0.25% cholesterol diet after the intervention. Early 7 day follow up (n=3 per group) or late 28 day follow-up (n=3 per group) animals underwent total-body perfusion-fixation as previously described with immediate excision of the aortic segment containing stent. The 7 day aortic specimens were excised longitudinally and stents were removed. The resulting aortic segments were divided into two equal subsegments. One subsegment of each underwent fixation in 10% neutral buffered formalin and embedded in paraffin for light microscopic and morphologic analysis. The remaining subsegment of each specimen was snap frozen for molecular assay. The 28 days aortic specimens were fixed in 10% neutral buffered formalin and were embedded in PolyBed (Polysciences, Warrington, Pa.) for light microscopic and morphologic analysis.

Morphological Analysis of Intima/Media (IIM) Ratios.

The seven day analysis consisted of thick (5 µm) cross sections of the aortic wall were obtained from the paraffin-embedded specimens (n=9 sections per group). An elastic von Gieson-Masson trichrome or Elastica van Gieson-Hematoxylin double stain was performed for light microscopic analysis. For the 28 day specimen analysis (n=3 animals per group), each plastic-embedded aorta with stents was cut into five pieces longitudinally equal lengths. These pieces were stained by modified Verhoff elastic staining. Five cross sectional images of the stained aorta were obtained (n=15 sections per group) from one side of plastic pieces. High resolution digital images of histological cross sections were acquired at 100X magnification from a Diagnostic Instruments SPOT true-color camera (Diagnostic Instruments, Sterling Heights, Mich.) as displayed on a Nikon E600 with Plan Apochromat Lenses (Nikon). Using Image Pro Plus software (Media Cybernetics, Silver Spring, Md.), the cross-sectional area of the intima and the media were determined by blinded observers. The ratio of intima area to media area subsequently tabulated for each, with the results presented as Table 2. Mean, standard error, and significance were determined.

TABLE 2

Plaque formation after in vivo stent implantation and angiostatin release.

| | Intima to media ratio |
|---|---|
| Control | 1.981 ± 0.080 |
| Angiostatin | 1.610 ± 0.050* |

Ratio of intimal area to medial area 28 days after stent implantation for control stents or stents releasing angiostatin (mean ± SE),
*denotes P = 0.003 vs. controls.

Evaluation of Local Plaque Stability Parameters: Macrophage Infiltrate and Endothelial Density.

Cross sections at the 7 day time point evaluated above were obtained (two per segment) from each vessel and incubated with a primary monoclonal antibody to rabbit macrophage (clone RAM-11, 1/800 dilution, DAKO, Carpinteria, Calif.). The number of positive cells per cross section was counted by a blinded observer. Endothelial cells were stained with CD-31 in order to evaluate endothelial cell density. Mean and standard error were tabulated for each group with significance determined as before and p values as reported. The results of both analyses are presented as Table 3.

TABLE 3

Plaque stability after in vivo stent implantation and angiostatin release.

| | Macrophages | CD31 |
|---|---|---|
| Control | 55.200 ± 3.837 | 4.889 ± 0.696 |
| Angiostatin | 34.889 ± 3.948* P = 0.0011 | 0.111 ± 0.111* |

Number of cross-sectional macrophages or plaque microvessels (CD31) 7 days after stent implantation for control stents or stents releasing angiostatin (mean ± SE),
*denotes P < 0.05 vs. controls.

Conclusions.

Stent based local release of an angiogenesis inhibitor reduces plaque progression after stenting and stabilizes the plaque that does form so that plaque rupture, occlusion, and adverse long-term outcome are reduced in frequency. While this example presents use of angiostatin as a specific agent, any anti-angiogenic factor could be substituted with comparable result (i.e. the example demonstrates efficacy of the class of agents).

EXAMPLE 3

Stent-based Release of a Factor to Increase Nitric Oxide Levels can Limit In-stent Plaque Progression Microsphere/stent Preparation.

Microspheres were prepared as above (example 2b) except loaded with 40 mg NOC-12 (Calbiochem, La Jolla, Calif.) in 200 µl phosphate buffered saline in place of angiostatin and stents were loaded as before.

Plaque Formation.

Plaque morphometry was assessed as in Example 2, with results summarized as Table 4.

TABLE 4

Plague formation after in vivo stent implantation and nitric oxide release.

| | Intima to media ratio |
|---|---|
| Control | 1.981 ± 0.080 |
| NO | 1.338 ± 0.051* |

Ratio of intimal area to medial area 28 days after stent implantation for control stents or stents releasing a nitric oxide donor (NO), (mean ± SE),
*denotes P = 0.0001 vs. controls.

Conclusions.

Stent based local release of a nitric oxide donor reduces plaque progression after stenting. While this example presents use of NOC-12 as a specific agent, any NO donor could be substituted with comparable result (i.e. the example demonstrates efficacy of the class of agents).

EXAMPLE 4

Stent-based Release of an Elastase (or Matrix Metalloproteinase) Inhibitor can Limit In-stent Plaque Progression Local prevention of post-stenting extracellular matrix remodeling can limit plaque progression.

Microsphere/stent Preparation.

Microspheres were prepared as above (Example 2) except loaded with 40 mg of the elastase inhibitor alpha-1-antitrypsin (Calbiochem, La Jolla, Calif.) in 200 µl phosphate buffered saline in place of angiostatin and stents were loaded as before.

Plaque Formation.

Plaque morphometry was assessed as in Example 2, with results summarized as Table 5.

TABLE 5

Plaque formation after in vivo stent implantation and release of an elastase inhibitor.

| | Intima to media ratio |
|---|---|
| Control | 1.981 ± 0.080 |
| AAT | 1.322 ± 0.060* |

Ratio of intimal area to medial area 28 days after stent implantation for control stents or stents releasing an elastase inhibitor (AAT), (mean ± SE),
*denotes P = 0.0001 vs. controls.

Conclusions.

Stent based local release of an inhibitor of extracellular matrix cleavage reduces plaque progression after stenting. While this example presents use of AAT as a specific agent, any factor to inhibit elastase or matrix metalloproteinases could be substituted with comparable-result (i.e. the example demonstrates efficacy of the class of agents).

EXAMPLE 5

Stent-based Release of Nicotine or Nicotinic Receptor Agonist Limits In-stent Plaque Progression Microsphere/stent Preparation.

Microspheres were prepared as above (Example 2) except loaded with 30.0 mg Nicotine (Sigma Chemical, St Louis, Mo.) (to achieve a calculated daily load release of 0.1 mg/ml) in 200 µl phosphate buffered saline in place of angiostatin and stents were loaded as before.

Plaque Formation.

Plaque morphometry was assessed as in Example 2, with results summarized as Table 6.

TABLE 6

Plaque formation after in vivo stent implantation and nicotine release.

| | Intima to media ratio |
|---|---|
| Control | 1.981 ± 0.080 |
| Nicotine | 1.377 ± 0.060* |

Ratio of intimal area to medial area 28 days after stent implantation for control stents or stents releasing nicotine (mean ± SE),
*denotes P = 0.0001 vs. controls.

Conclusions.

Stent based local release of nicotine reduces plaque progression after stenting.

EXAMPLE 6

Stent-based Release of Transforming Growth Factor β can Limit In-stent Plaque Progression Microsphere/stent Preparation.

Microspheres were prepared as above, except loaded with 2.0 µg TGFβ1 (Oncogene Research, Boston, Mass.) in 200 µl phosphate buffered saline in place of angiostatin and stents were loaded as before.

Plaque Formation.

Plaque morphometry was assessed as above, with results summarized as Table 7.

TABLE 7

Plaque formation after in vivo stent implantation and TGFβ1 release.

| | Intima to media ratio |
|---|---|
| Control | 1.981 ± 0.080 |
| TGFβ1 | 1.803 ± 0.053* |

Ratio of intimal area to medial area 28 days after stent implantation for control stents or stents releasing transforming growth factor β1 (TGFβ1), (mean ± SE),
*denotes P = 0.004 vs. controls.

Stent based local release of transforming growth factor β or other agonist of transforming growth factor β receptors or downstream signaling reduces plaque progression after stenting.

EXAMPLE 7

Stent-based Release of an Angiotensin Pathway Inhibitor

Release of an inhibitor of angiotensin converting enzyme, angiotensin, angiotensin II, or angiotensin II receptors can limit in-stent plaque progression.

Microsphere/Stent Preparation.

Microspheres were prepared as above except loaded with 1.2 mg of the angiotensin II receptor inhibitor perindoprilate in 200 µl phosphate buffered saline in place of angiostatin and stents were loaded as before.

Plaque Formation.

Plaque morphometry was assessed as above, with results summarized as Table 8.

TABLE 8

Plaque formation after in vivo stent implantation and release of an angiotensin II receptor inhibitor.

| | Intima to media ratio |
|---|---|
| Control | 1.981 ± 0.080 |
| ATIIr | 1.730 ± 0.090* |

Ratio of intimal area to medial area 28 days after stent implantation for control stents or stents releasing of an angiotensin II receptor inhibitor, (ATIIr), (mean ± SE),
*denotes P = 0.02 vs. controls.

Stent based local release of an inhibitor of angiotensin converting enzyme, angiotensin, angiotensin II, or angiotensin II receptors or downstream signaling reduces plaque progression after stenting.

EXAMPLE 8

Stent-based Release of a Pro-apoptotic Factor

Microsphere/stent Preparation.

Microspheres were prepared as above except loaded with 10 µg Fas ligand (Oncogene Research, Boston, Mass.) in 200 µl phosphate buffered saline in place of angiostatin and stents were loaded as before.

Plaque Formation.

Plaque morphometry was assessed as above, with results summarized as Table 9.

TABLE 9

Plaque formation after in vivo stent implantation and release of Fas ligand.

|  | Intima to media ratio |
|---|---|
| Control | 1.981 ± 0.080 |
| Fas ligand | 1.356 ± 0.053* |

Ratio of intimal area to medial area 28 days after stent implantation for control stents or stents releasing Fas Ligand, (mean ± SE), *denotes P < 0.05 vs. controls.

Stent based local release of a pro-apoptotic factor such as fas-ligand reduces plaque progression after stenting. While this example presents use of Fas ligand as a specific agent, any pro-apoptotic factor could be substituted with comparable result (i.e. the example demonstrates efficacy of the class of agents).

EXAMPLE 9

Stent-based Release of Fibroblast Growth Factor

Microsphere/stent Preparation.
Microspheres were prepared as above except loaded with 200 ng acidic FGF (Calbiochem, La Jolla, Calif.) and 1280 units filtered endotoxin-free heparin (Sigma Chemical, St Louis, Mo.) as a stabilizer in 200 µl phosphate buffered saline in place of angiostatin and stents were loaded as before.

Plaque Formation.
Plaque morphometry was assessed as above, with results summarized as Table 10.

TABLE 10

Plaque formation after in vivo stent implantation and release of acidic FGF.

|  | Intima to media ratio |
|---|---|
| Control | 1.981 ± 0.080 |
| FGF | 1.634 ± 0.051* |

Ratio of intimal area to medial area 28 days after stent implantation for control stents or stents releasing of acidic FGF, (FGF), (mean ± SE), *denotes P = 0.004 vs. controls.

Stent based local release of fibroblast growth factor (acidic or basic, with or without heparin), any pro-endothelialization growth factor or related downstream signaling reduces plaque progression after stenting.

EXAMPLE 11

Stent-Based Release of Thrombin Pathway Inhibitors

Microsphere/Stent Preparation.
Microspheres are prepared as above, except loaded with D-Phe-Pro-Arg chloromethyl ketone (PPACK, Calbiochem), which is the prototype of a class of synthetic tripeptides that form covalent complexes with thrombin, (Calbiochem, La Jolla, Calif.) in 200 µl phosphate buffered saline in place of angiostatin. PPACK irreversibly inhibits thrombin by alkylating the active center histidine residue. Since thrombin and thrombin receptor-activating peptide (TRAP)-induced DNA synthesis are potently inhibited by PD98059 (Calbiochem, La Jolla, Calif.), an inhibitor of ERK phosphorylation, this inhibitor or others of its class can be used alone or in combination to inhibit thrombin-mediated plaque progression after stenting. PD98059 is examined in the range from 100 nmol/l to 500 µmol/L daily release (optimal typically in the range of 10 µmol/L). PPACK is evaluated in a range from 0.1 nmol/L to 10 µmol/L daily release (with typical use at 10 nmol/L in vitro).

Plaque Formation.
Plaque morphometry is assessed as above.

EXAMPLE 12

Stent-based Gene Transfer

Microsphere/stent Preparation.
Microspheres were prepared as above (example 2) except loaded with 200 µl of a 1.0 mg/ml solution of a plasmid encoding E. coli beta-galactosidase as a marker under the control of the cytomegalovirus promoter with a 2:1 charge ratio of Superfect (400 µl of stock 1.2 mg/ml, Qiagen) added as a transfection agent (10 µl undiluted) (Calbiochem, La Jolla, Calif.) in 200 µl phosphate buffered saline in place of angiostatin.

Gene Expression.
Gene expression was confirmed functionally on cross-sections obtained as for plaque morphometry 7 days after stent deployment. Beta galactosidase expression was visualized using X-gal staining (Sigma, St. Louis, Mo.) and showed specific staining.

Conclusions.
Stent-based gene transfer of DNA, RNA, ribozyme, hybrids, or derivatives can be afforded at levels to achieve therapeutic benefit. While this example presents use of beta-galactosidase as a specific agent, any DNA, RNA, ribozyme, hybrid, or derivative could be substituted alone or in combination with comparable result (i.e. the example demonstrates efficacy of the class of agents).

EXAMPLE 13

Stent-based Gene Transfer to Limit Plaque Progression

Microsphere/stent Preparation.
Microspheres are prepared as above except loaded with 20 µl of a 1.0 mg/ml solution of a plasmid encoding human thrombomodulin under the control of the cytomegalovirus promoter with a 4:1 charge ratio of Superfect added as a transfection agent (10 µl undiluted) (Calbiochem, La Jolla, Calif.) in 200 µl phosphate buffered saline in place of angiostatin.

Plaque Formation.
Plaque morphometry is assessed as above, with gene expression also confirmed antigenically or functionally.

EXAMPLE 14

Stent-based Delivery of Passively Entangled Noncovalently Bound Rapamycin to Limit Plaque Progression Stent Preparation.
BX-velocity stents (Cordis, Miami, Fla.) are derivatized as above with a silane linker. The stent is placed within an outer tube which rests flush against the stent outer surface and is open at either end. A glycerol solution or other viscous solution is instilled to fill all spaces. The glycerol is allowed to drain by gravity and the stent is washed and immediately drained with sterile water, allowing some traces of glycerol to remain at the stent-tube interface. The outer surface of the stent and the adjacent sites are thus blocked from incubation, as a solution with a polymerization chain blocker or terminator is instilled and linked to the exposed surface of the stent. In the present case, such a terminator is polyethylene glycol (PEG) monoacrylate (MW200), which is anchored under exposure to UV-A source for 15 minutes. The stent is then removed from the cylinder and washed repeatedly to remove glycerol and unreacted chain blocker. The stent is then immersed in a sterile highly viscous solution containing PEG (MW 8000), PEG dimethacrylate (MW1200), and star-polymer PEG multi-methacrylates together with rapamycin at an effective dose for post-stenting restenosis. The stent is placed within an outer tube which allows a gap of 30 microns between the stent and the inner wall of the cylinder (although other thicknesses are valid as well). The gel is then polymerized under UV-A for 30 minutes to anchor rapamycin passively to the outer surface of the stent and the shoulders of the stent. Unreacted solution is removed by washing and the stent is lyophillized for use.

Plaque Formation.

Plaque morphometry is assessed as above, with gene expression also confirmed antigenically or functionally.

EXAMPLE 15

Stent-based Delivery of Chelated Noncovalently Bound Rapamycin to Limit Plaque Progression Stent Preparation.

BX-velocity stents (Cordis, Miami, Fla.) are derivatized as above with a silane linker. The stent is placed within an outer tube which rests flush against the stent outer surface and is open at either end. A glycerol solution or other viscous solution is instilled to fill all spaces. The glycerol is allowed to drain by gravity and the stent is washed and immediately drained with sterile water, allowing some traces of glycerol to remain at the stent-tube interface. The outer surface of the stent and the adjacent sites are thus blocked from incubation, as a solution with a polymerization chain blocker or terminator is instilled and linked to the exposed surface of the stent. In the present case, such a terminator is polyethylene glycol (PEG) monoacrylate (MW200), which is anchored under exposure to UV-A source for 15 minutes. The stent is then removed from the cylinder and washed repeatedly to remove glycerol and unreacted chain blocker. The stent is then immersed in a highly viscous solution containing PEG (MW 8000), PEG dimethacrylate (MW1200), and a carrier which contains a methacrylate link and self assembles to chelate and carry rapamycin via some combination of ionic, hydrogen bonds, and van der waals forces together with rapamycin at an effective dose for post-stenting restenosis. The gel is then polymerized under UV-A for 30 minutes to anchor rapamycin passively to the outer surface of the stent and the shoulders of the stent. Unreacted solution is removed by washing and the stent is lyophillized for use.

Plaque Formation.

Plaque morphometry is assessed as above, with gene expression also confirmed antigenically or functionally.

EXAMPLE 14

Stent-based Delivery of Noncovalently Bound Rheopro to Limit Plaque Progression

Stent Preparation.

BX-velocity stents (Cordis, Miami, Fla.) are derivatized as above with a silane linker. The stent is placed within an outer tube which rests flush against the stent outer surface and is open at either end. A glycerol solution or other viscous solution is instilled to fill all spaces. The glycerol is allowed to drain by gravity and the stent is washed and immediately drained with sterile water, allowing some traces of glycerol to remain at the stent-tube interface. The outer surface of the stent and the adjacent sites are thus blocked from incubation, as a solution with a polymerization chain blocker or terminator is instilled and linked to the exposed surface of the stent. In the present case, such a terminator is polyethylene glycol (PEG) monoacrylate (MW200), which is anchored under exposure to UV-A source for 15 minutes. The stent is then removed from the cylinder and washed repeatedly to remove glycerol and unreacted chain blocker. The stent is then immersed in a sterile highly viscous solution containing PEG (MW 8000), PEG dimethacrylate (MW1200), and star-polymer PEG multi-methacrylates together with RheoPro at an effective dose for post-stenting restenosis. The stent is placed within an outer tube which allows a gap of 30 microns between the stent and the inner wall of the cylinder (although other thicknesses are valid as well). The gel is then polymerized under UV-A for 30 minutes to anchor RheoPro passively to the outer surface of the stent and the shoulders of the stent. Unreacted solution is removed by washing and the stent is lyophillized for use.

Plaque Formation.

Plaque morphometry is assessed as above, with gene expression also confirmed antigenically or functionally.

What is claimed is:

1. A platform for localized delivery of a biologically active agent, comprising:
   a stent comprising channels on one or both of the adluminal and abluminal surfaces, wherein contained within said channels is a matrix of microspheres in which a biologically active agent is entrapped; said stent being ensheathed in a gel covalently bound to the stent surface, which gel fills unoccupied spaces within the channels and between said microspheres.

2. The platform according to claim 1, wherein said gel is additionally covalently bound to said matrix.

3. The platform according to claim 1, wherein said stent is formed of a biologically compatible metal.

4. The platform according to claim i, wherein said stent is a polymeric biodegradable or erodible stent.

5. The platform according to claim i, wherein said channels are from 10 to 200 µm in depth.

6. The platform according to claim 5, wherein said channels extend end to end, or the entire circumference of the stent.

7. The platform according to claim 5, wherein said channels are adluminal.

8. The platform according to claim 5, wherein said channels are abluminal.

9. The platform according to claim 5, wherein said channels are at least about 10 µm in width.

10. The platform according to claim 5, wherein said channels are tapered.

11. The platform according to claim 1, wherein said stent surface is modified with an adhesion agent for covalent binding.

12. The platform according to claim 11, wherein said stent is comprised of a biologically compatible metal, and said adhesion agent is a silane coupling reagent.

13. The platform according to claim 1, wherein said particles are microspheres of about 1 to 100 µm in diameter.

14. The platform according to claim 1, wherein said matrix is covalently bound to said gel.

15. The platform according to claim 1, wherein said matrix is comprised of a biodegradable polymer.

16. The platform according to claim 14, wherein said biodegradable polymer comprises one or more of D-lactic acid, L-lactic acid, racemic lactic acid, glycolic acid and polycaprolactone.

17. The platform according to claim 1, wherein said matrix is comprised of a biocompatible, non-biodegradable polymer.

18. The platform according to claim 1, wherein said gel comprises methacrylate.

19. The platform according to claim 1, wherein said biologically active agent is a pharmacologically active drug.

20. The platform according to claim 1, wherein said biologically active agent is a protein.

21. The platform according to claim 1, wherein said biologically active agent is a nucleic acid.

22. The platform according to claim 1, wherein said biologically active agent inhibits in-stent restenosis.

23. The platform according to claim 22, wherein said biologically active agent is rapamycin.

24. The platform according to claim 22, wherein said biologically active agent is an inhibitor of GPIIb/IIIa.

25. The platform according to claim 24, wherein said inhibitor is RheoPro.

26. A method for localized delivery of a biologically active agent, comprising:
   implanting in the lumen of a vessel a stent comprising channels on one or both of the adluminal and abluminal surfaces, wherein contained within said channels is a matrix of microspheres in which a biologically active agent is entrapped; said stent being ensheathed in a gel covalently bound to the stent surface; which gel fills unoccupied spaces within the channels and between said microspheres;
   wherein said biologically active agent is released from said matrix.

27. The method according to claim 26, wherein said matrix is covalently bound to said gel.

28. The method according to claim 26, wherein said stent is formed of a biologically compatible metal.

29. The method according to claim 26, wherein said stent is a polymeric biodegradable or erodible stent.

30. The method according to claim 26, wherein said channels are from 10 to 200 μm in depth.

31. The method according to claim 26, wherein said channels extend end to end, or the entire circumference of the stent.

32. The method according to claim 30, wherein said channels are adluminal.

33. The method according to claim 30, wherein said channels are abluminal.

34. The method according to claim 30, wherein said channels are at least about 10 μm in width.

35. The method according to claim 30, wherein said stent surface is modified with an adhesion agent for covalent binding.

36. The method according to claim 35, wherein said stent is comprised of a biologically compatible metal, and said adhesion agent is a silane coupling reagent.

37. The method according to claim 27, wherein said particles are microspheres of about 1 to 100 μm in diameter.

38. The method according to claim 27, wherein said matrix is comprised of a biodegradable polymer.

39. The method according to claim 38, wherein said biodegradable polymer comprises one or more of D-lactic acid, L-lactic acid, racemic lactic acid, glycolic acid and polycaprolactone.

40. The method according to claim 27, wherein said matrix is comprised of a biocompatible, non-biodegradable polymer.

41. The method according to claim 26, wherein said gel comprises methacrylate.

42. The method according to claim 26, wherein said biologically active agent is a pharmacologically active drug.

43. The method according to claim 26, wherein said biologically active agent is a protein.

44. The method according to claim 26, wherein said biologically active agent is a nucleic acid.

45. The method according to claim 26, wherein said biologically active agent inhibits in-stent restenosis.

46. The method according to claim 45, wherein said biologically active agent is rapamycin.

47. The method according to claim 45, wherein said biologically active agent is an inhibitor of GPIIb/IIIa.

48. The method according to claim 46, wherein said inhibitor is RheoPro.

* * * * *